United States Patent [19]

Inoue et al.

[11] Patent Number: 5,744,630
[45] Date of Patent: Apr. 28, 1998

[54] METHOD OF PRODUCING 3-AMINO-2-HYDROXY-1-PROPANOL DERIVATIVES

[75] Inventors: Kenji Inoue, Kakogawa; Hiroshi Awaji, Akashi; Satomi Takahashi, Kobe, all of Japan

[73] Assignee: Kaneka Corporation, Osaka, Japan

[21] Appl. No.: 436,344

[22] PCT Filed: Sep. 20, 1994

[86] PCT No.: PCT/JP94/01540

§ 371 Date: Jul. 18, 1995

§ 102(e) Date: Jul. 18, 1995

[87] PCT Pub. No.: WO95/08530

PCT Pub. Date: Mar. 30, 1995

[30] Foreign Application Priority Data

Sep. 20, 1993 [JP] Japan .................. 5-233240

[51] Int. Cl.⁶ .................. C07D 263/20
[52] U.S. Cl. .................. 560/29; 548/232; 564/336; 564/355; 564/473
[58] Field of Search .................. 568/846; 564/336, 564/473, 506, 507; 560/29

[56] References Cited

U.S. PATENT DOCUMENTS

| | | | |
|---|---|---|---|
| 4,219,508 | 8/1980 | Wagner | 564/473 |
| 4,933,511 | 6/1990 | Gredley et al. | 568/846 |
| 5,220,020 | 6/1993 | Buchwald et al. | 568/846 |
| 5,367,094 | 11/1994 | Chung | 560/29 |
| 5,399,763 | 3/1995 | Satoh et al. | 564/506 |
| 5,556,516 | 9/1996 | Koyama | 564/846 |
| 5,659,065 | 8/1997 | Goschke | 560/29 |

FOREIGN PATENT DOCUMENTS

| | | |
|---|---|---|
| 3-44363 | 2/1991 | Japan . |
| 95-08530 | 3/1995 | Japan . |

OTHER PUBLICATIONS

Park et al., Practical Hydroxymethylation of Aldehydes and Ketones via Pinacol Cross–Coupling Reactions with Paraformaldehyde, Tetrahedron, vol. 48, No. 11, 1992, pp. 2069–2080.

*Primary Examiner*—Donald G. Daus
*Attorney, Agent, or Firm*—Pollock, Vande Sande & Priddy

[57] ABSTRACT

The present invention has for its object to provide an efficient and economical method for producing an 3-amino-2-hydroxy-1-propanol derivative and an oxazolidinone derivative derived therefrom, both of which are of use as intermediates for the production of drugs including HIV protease inhibitors.

The invention relates to a method for producing an 3-amino-2-hydroxy-1-propanol derivative of general formula (2)

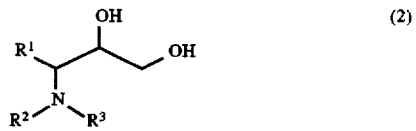

(wherein $R^1$ represents alkyl, aralkyl or aryl; $R^2$ and $R^3$ independently represent hydrogen or an amino-protecting group, provided, however, that both $R^2$ and $R^3$ are not concurrently hydrogen) and an oxazolidinone derivative derived therefrom.

6 Claims, No Drawings

5,744,630

METHOD OF PRODUCING 3-AMINO-2-HYDROXY-1-PROPANOL DERIVATIVES

TECHNICAL FIELD

The present invention relates to efficient processes for producing an 3-amino-2-hydroxy-1-propanol derivative of the following general formula (2) and an oxazolidinone derivative of the following general formula (5), both of which are of value as intermediates for the production of medicines.

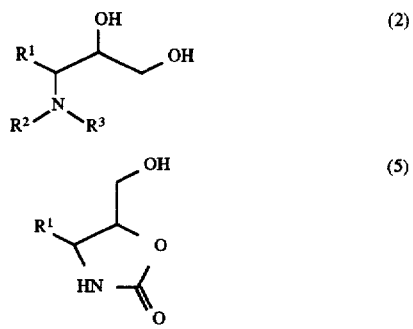

wherein $R^1$ represents alkyl, aralkyl or aryl; $R^2$ and $R^3$ independently represent hydrogen or an amino-protecting group; provided, however, that both $R^2$ and $R^3$ are not concurrently hydrogen.

In particular, optically active 3-amino-2-hydroxy-1-propanol derivatives and oxazolidinone derivatives derived therefrom are of value as intermediates for the production of the HIV protease inhibitor.

PRIOR ART

The following processes are already known for the production of 3-amino-2-hydroxy-1-propanol derivatives of general formula (2) and oxazolidinone derivatives of general formula (5) which are derivable therefrom.

(A) A process starting with L-ascorbic acid or D-isoascorbic acid and involving formation of an azide compound (Bulletin de la Societe Chimique de France, 129, 585, 1992).

(B) A process in which paraformaldehyde and N-tosylvalinal are subjected to coupling reaction in the presence of vanadium trichloride and zinc (Tetrahedron 48, 2069, 1992).

(C) A process involving iodocyclocarbamylation of an N-(benzyloxycarbonyl)allylamine derivative (Tetrahedron Letters 25, 5079, 1984).

However, among the above processes, the first-mentioned process (A) utilizing the azide compound has the disadvantage that it requires not only costly reagents but also many processing steps. The third-mentioned process (C) utilizing an N-(benzyloxycarbonyl)allylamine also requires expensive reagents and many processing steps. The second process (B) utilizing vanadium trichloride involves a comparatively short reaction procedure but is disadvantageous in that the indispensable reducing agent vanadium trichloride is comparatively expensive and that when applied to N-tosylvarinal which is the exclusive compound described in the examples of synthesis of 3-amino-2-hydroxy-1-propanol derivatives, the process hardly provides for stereoselectivity.

Thus, the processes thus far known have many disadvantages to be overcome for commercial production of 3-amino-2-hydroxy-1-propanol derivatives or oxazolidinone derivatives derivable therefrom, thus being neither efficient nor economical for commercial application.

DISCLOSURE OF THE INVENTION

Developed in view of the above state of the art, it is an object of the present invention to provide an efficient and economical method for producing 3-amino-2-hydroxy-1-propanol derivatives and oxazolidinone derivatives derivable therefrom.

After intensive research, the inventors of the present invention found that as an aminoaldehyde derivative whose amino group has been protected and a formaldehyde source compound are subjected to hetero-coupling reaction with the aid of a low valence titanium, the objective 3-amino-2-hydroxy-1-propanol derivative can be obtained in a short sequence of steps and that where the amino-protecting group of said aminoaldehyde derivative is an ester residue such as benzyloxycarbonyl or t-butoxycarbonyl, a 4-substituted-5-hydroxymethyloxazolidinone derivative can be obtained by treating said coupling reaction product further with a base. The present invention has been developed on the basis of the above findings.

The present invention, therefore, is directed, in a first aspect, to a process for producing an 3-amino-2-hydroxy-1-propanol derivative of general formula (2):

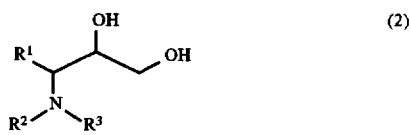

(wherein $R^1$, $R^2$ and $R^3$ are as defined below) which comprises reacting an aminoaldehyde derivative of general formula (1):

(wherein $R^1$ represents alkyl, aralkyl or aryl; $R^2$ and $R^3$ independently represent hydrogen or an amino-protective group; provided, however, that both $R^2$ and $R^3$ are not concurrently hydrogen) by hetero-coupling reaction with a formaldehyde source in the presence of a low valence titanium.

The present invention is further directed, in a second aspect, to a process for producing an oxazolidinone derivative of general formula (5):

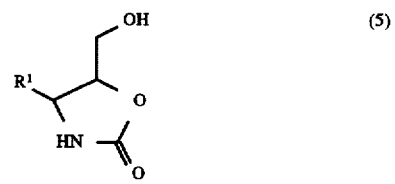

(wherein $R^1$ is as defined hereinbefore) which comprises reacting an aminoaldehyde derivative of general formula (3):

(wherein $R^1$ is as defined hereinbefore; R' represents an ester residue) with a formaldehyde source by hetero-coupling reaction in the presence of a low valence titanium to give an alcohol derivative of general formula (4):

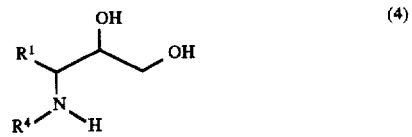

(4)

(wherein $R^1$ and $R^4$ are as defined hereinbefore) and, then, subjecting said alcohol derivative to cyclization reaction with the aid of a base.

$R^1$ in the above general formulas (1) et seq. is not particularly restricted in kind, thus including alkyl groups such as methyl, ethyl, isopropyl, etc., aralkyl groups such as benzyl, β-phenylethyl, 3-phenylpropyl, etc., and aryl groups such as phenyl, p-hydroxyphenyl, m-chlorophenyl, etc.

Referring further to the above general formulas (1) et seq., $R^2$ and $R^3$ independently represent hydrogen or an amino-protecting group. However, compounds in which both $R^2$ and $R^3$ are concurrently hydrogen are excluded from the present invention.

The amino-protecting group mentioned above is not particularly restricted in kind, thus including the variety of protective groups mentioned in inter alia Theodora W. Green: Protective Groups in Organic Synthesis, 2nd Ed., John Wiley and Sons, 309–384 (1990), viz. benzyloxycarbonyl, formyl, acetyl, trifluoroacetyl, benzyl, phthalimido, tosyl, t-butoxycarbonyl, ethoxycarbonyl, benzoyl and so on. Among them, ester residues such as benzyloxycarbonyl, t-butoxycarbonyl, ethoxycarbonyl, etc., acyl groups such as acetyl, benzoyl, etc., and phthalimido are preferred.

$R^4$ in the above general formulas (3) et seq. represents an ester residue. This ester residue is not particularly restricted in kind, thus including benzyloxycarbonyl, t-butoxycarbonyl, ethoxycarbonyl, and so on. Among them, benzyloxycarbonyl and t-butoxycarbonyl are preferred.

There is no restriction on the technology that can be used for preparing the compound of general formula (1) or the compound of general formula (3). For example, it can be prepared by the process comprising protecting the amino group of an amino acid in the conventional manner, then esterifying the carbonyl group, and finally reducing the same, and the process comprising reducing the carbonyl group of an N-protected amino acid derivative to the corresponding alcohol in the first place and, then, oxidizing the alcohol to the aldehyde.

The formaldehyde source that is used in the coupling reaction of the compound of general formula (1) or the compound of general formula (3) includes paraformaldehyde, formalin, trioxane and polyoxymethylene, among others. In the method of the present invention, said formaldehyde source is used in a proportion of 1 to 50 molar equivalents, preferably 10 to 20 molar equivalents, relative to the compound of general formula (1) or the compound of general formula (3).

The titanium formed by, for example, reducing $TiCl_4$ or $TiCl$, with Zn, Zn—Cu, Mg or Al within the reaction system of the present invention can be used as the low valence titanium for the present invention. In the practice of the present invention, said $TiCl_4$ or $TiCl_3$ is used in a proportion of 0.1 to 5 molar equivalents, preferably 0.5 to 3 molar equivalents, and for still better results, 1 to 2 molar equivalents, relative to the compound of general formula (1) or the compound of general formula (3).

In the practice of the present invention, Zn, Zn—Cu, Mg or Al may be preferably used in a proportion of 1 to 6 molar equivalents, more preferably 2 to 3 molar equivalents, relative to the compound of general formula (1) or the compound of general formula (3).

The reaction solvent for use in the present invention is not particularly restricted in kind. Thus, for example, aprotic solvents such as TEF (tetrahydrofuran), DME (1,2-dimethoxyethane), dioxane, methylene chloride, chloroform, ethyl acetate, etc. can be used with advantage. The amount of the solvent is such that the concentration of the compound of general formula (1) or the compound of general formula (3) will be 1 to 20 w/v %, preferably 3 to 10 w/v %.

A typical reaction procedure in accordance with the present invention using paraformaldehyde as said formaldehyde source and $TiCl_4$ in combination with Zn as said low valence titanium comprises adding $TiCl_4$ and Zn in that order to a THF solution of paraformaldehyde at a temperature of $-50°$ to $0°$ C., preferably $-30°$ to $-10°$ C. and, then, adding a THF solution of the compound of general formula (1) or the compound of general formula (3) gradually at room temperature. An alternative reaction procedure comprises adding a THF solution of either the compound of general formula (1) or the compound of general formula (3) and $TiCl_4$ concurrently and gradually to a THF solution containing paraformaldehyde and Zn at a temperature of $-10°$ to $40°$ C., preferably $0°$ to $30°$ C.

The after-treatment following the above reaction according to the present invention is not particularly restricted. Thus, for example, the reaction mixture on completion of the above reaction is quenched with aqueous sodium hydrogen carbonate solution and, then, filtered to remove insoluble matter. The filtrate is extracted or concentrated in the conventional manner and purified by column chromatography or crystallization.

The reaction temperature, the manner of addition of reagents, after-treatment, and other particulars are not necessarily limited to those mentioned above. Thus, the present invention can be carried into practice by various other alternative procedures.

Where the compound of general formula (1) or the compound of general formula (3) is optically active, the resulting product of general formula (2) or compound of general formula (4) occurs in two configurational isomers, namely threo-and erythro-forms. The stereochemical specificity of this reaction may vary with the structure of the compound of general formula (1) or the compound of general formula (3) and the reaction conditions employed but, as far as the present invention is concerned, usually, the erythro-form is preferentially formed.

For example, when L-N-(benzyloxycarbonyl) phenylalaninal is used as said compound of general formula (1), the erythro compound, (2S,3S)-3-(benzyloxycarbonylamino)-4-phenylbutane1,2-diol tend to be produced preferentially as the compound of general formula (2). This compound is of value as an intermediate of HIV protease inhibitors.

The compound of general formula (4) as produced by the coupling reaction in accordance with the present invention can be easily transformed to a 4-substituted-5-hydroxymethyloxazolidinone derivative of general formula (5) by treating the compound (4) with a base to induce an intramolecular cyclization reaction. The base for use in the above reaction is not particularly restricted in kind, thus including sodium hydride, sodium methoxide, sodium ethoxide, potassium t-butoxide, sodium hydroxide and potassium hydroxide, among other bases. The recommended amount of said base is 0.1 to 3 molar equivalents, preferably 1 to 2 molar equivalents, relative to the compound of general formula (4).

The reaction solvent for the above cyclization reaction can be liberally selected according to the base employed. For example, where the base is sodium hydride, an aprotic solvent such as THF, DME and dioxane is preferred. Where the base is sodium hydroxide or potassium hydroxide, for instance, it is preferable to use water alone, a mixture of water and an organic solvent, e.g. methanol, ethanol or THF, or an alcohol, e.g. methanol or ethanol, alone. The amount of said reaction solvent is preferably such that the concentration of the compound of general formula (4) will be 1 to 30 w/v % and, for still better results, 5 to 20 w/v %.

The reaction temperature for the above cyclization reaction is −20° to −50° C. and preferably −10° to −30° C.

The after-treatment following the above reaction of this invention is not particularly restricted in kind. A typical procedure comprises quenching the reaction mixture, after the above reaction procedure, using ammonium chloride, for instance, and purifying and isolating the objective compound by the conventional procedure such as extraction or concentration followed by column chromatography or crystallization.

The reaction temperature, the manner of addition of reagents, after-treatment, and other particulars of the reaction are not necessarily limited to those described above but the present invention can be carried into practice by various other procedures.

BEST MODE OF PRACTICING THE INVENTION

The following examples are intended describe the present invention in further detail and should by no means be construed as defining the scope of the invention.

EXAMPLE 1

Production of (2S,3S)-3-(benzyloxycarbonylamino)-4-phenylbutane-1,2-diol

To a solution containing 15 g (500 mmols) of paraformaldehyde in 150 ml of THF was added 4.14 ml of TiCl$_4$ gradually at −30° C. Then, 4.9 g of zinc dust was further added. The temperature was allowed to rise up to room temperature over 40 minutes, after which a solution prepared by dissolving 7.1 g of (25 mmols) of L-N-(benzyloxycarbonyl) phenylalaninal in 50 ml of THF was added dropwise over 2 hours. After completion of the dropwise addition, the mixture was further stirred for 20 minutes. Then, 50 ml of saturated aqueous sodium hydrogen carbonate solution was added and the reaction mixture was stirred at room temperature for 10 hours. The insoluble matter was then filtered off. The THF was then removed by concentration under reduced pressure and the residue was extracted with methylene chloride. The extract was dried over anhydrous sodium sulfate, filtered, and concentrated under reduced pressure to give 6.093 g of oil. This oil was purified by crystallizing from ethyl acetate to provide 1.68 g (5.37 mmols, yield 21.7%) of (2S,3S)-3-(benzyloxycarbonylamino)-4-phenylbutane-1,2-diol.

$^1$H-NMR (CDCl$_3$)δ/ppm: 2.80–2.92 (m, 2H), 3.05–3.20 (m, 2H), 3.35–3.48 (m, 1H), 3.55–3.72 (m, 2H), 3.85–3.92 (m, 1H), 4.82 (brd, 1H, 7.8 Hz), 4.98–5.10 (m, 2H), 7.15–7.38 (m, 10H)

IR (KBr)cm$^{-1}$: 3321, 1688, 1545, 1267, 1061, 1026

EXAMPLE 2

Production of (2S,3S)-3-(benzyloxycarbonylamino)-4-phenylbutane-1,2-diol

To a solution of 7.5 g (250 mmols) of paraformaldehyde and 8.18 g (125 mmols) of zinc in 86 ml of THF was added 0.48 g (5 mmols) of methanesulfonic acid and the mixture was stirred at 25° C. for 2 hours. Then, a solution containing 7.1 g (25 mmols) of L-N-(benzyloxycarbonyl) phenylalaninal in 56 ml of THF and 6.88 ml (62.5 mmols) of TiCl$_4$ were concurrently added gradually over 3 hours at a controlled internal temperature of 20° to 25° C. The mixture was further stirred at an internal temperature of 20° to 25° C. for 1 hour, at the end of which time 31.5 g of sodium hydrogen carbonate and 70 ml of water were added to the reaction mixture. This mixture was then stirred at room temperature for 10 hours, after which it was allowed to separate into layers. The aqueous layer was extracted with 100 ml of ethyl acetate and the organic layers were combined, dried over anhydrous sodium sulfate, filtered, and concentrated under reduced pressure to give 8.6 g of oil. This oil was purified by silica gel column chromatography (hexane/ethyl acetate=3/1) to provide 3.23 g (10.25 mmols, yield 41%) of (2S,3S)-3-(benzyloxycarbonylamin o)-4-phenylbutane-1,2-diol.

The spectrometric data of this compound were in good agreement with those of the compound of Example 1.

EXAMPLE 3

Production of (2S,3S)-3-(benzyloxycarbonylamino)-4-phenylbutane-1,2-diol

To a solution containing 0.494 ml of TiCl$_4$ and 20 ml of THF was added 1.2 g of Zn at −20° C. Then, the temperature was allowed to return to room temperature over 30 minutes, after which 1.80 g of paraformaldehyde was added. To this was added a solution containing 0.849 g (3 mmol) of L-N-(benzyloxycarbonyl)phenylalaninal in 25 ml of THF dropwise over 1 hour. The mixture was further stirred at room temperature for 3 hours, at the end of which time 30 ml of saturated aqueous sodium hydrogen carbonate solution was added. The reaction mixture was stirred at room temperature for 10 hours and the insoluble matter was filtered off. The filtrate was concentrated under reduced pressure to remove THF and the residue was extracted with methylene chloride. The extract was dried over anhydrous sodium sulfate, filtered, and concentrated under reduced pressure to give 0.902 g of oil. This oil was purified by crystallizing from ethyl acetate to provide 0.388 g (1.23 mmols, yield 41.0%) of (2S,3S)-3-(benzyloxycarbonylamino)-4-phenylbutane-1,2-diol.

The spectrometric data of this compound were in good agreement with those of the compound of Example 1.

EXAMPLE 4

Production of (2R,3R)-3-(benzyloxycarbonylamino)-4-phenylbutane-1,2-diol

The reaction procedure of Example 1 was repeated except that 7.1 g (25 mmols) of D-N-(benzyloxycarbonyl) phenylalaninal was used in lieu of 7.1 g (25 mmols) of L-N-(benzyloxycarbonyl)phenylalaninal and the reaction product was purified by crystallizing from ethyl acetate to provide 1.886 g (5.98 mmols, yield 23.9%) of (2R,3R)-3-(benzyloxycarbonylamino)-4-phenylbutane-1,2-diol.

$^1$H-NMR (CDCl$_3$)δ/ppm: 2.80–2.92 (m, 2H), 3.05–3.23 (m, 2H), 3.35–3.50 (m, 1H), 3.53–3.72 (m, 2H), 3.85–3.90 (m, 1H), 4.82 (brd, 1H, 7.8 Hz), 4.98–5.12 (m, 2H), 7.15–7.38 (m, 10H)

IR (KBr)cm$^{-1}$: 3320, 1690, 1545, 1269, 1060, 1025

EXAMPLE 5

Production of (2R,3R)-3-(benzyloxycarbonylamino)-4-phenylbutane-1,2-diol

The reaction procedure of Example 2 was repeated except that 7.1 g (25 mmols) of D-N-(benzyloxycarbonyl) phenylalaninal was used in lieu of 7.1 g (25 mmols) of L-N-(benzyloxycarbonyl)phenylalaninal and the reaction product was purified by silica gel column chromatography (hexane/ethyl acetate=3/1) to provide 3.23 g (10.25 mmols, yield 41%) of (2R,3R)-3-(benzyloxycarbonylamino)-4-phenylbutane-1,2-diol.

The spectrometric data of this compound were in good agreement with those of the compound of Example 4.

EXAMPLE 6

Production of (2S,3S)-3-(t-butoxycarbonylamino)-4-phenylbutane-1,2-diol

To a solution containing 6 g (200 mmols) of paraformaldehyde, 6.54 g (100 mmol) of zinc in 50 ml of THF, a solution containing 4.99 g (20 mmols) of L-N-(t-butoxycarbonyl)phenylalaninal in 50 ml of THF and 5.5 ml (50 mmols) of $TiCl_4$ were concurrently added gradually over 2 hours while the internal temperature was controlled at 10° to 15° C. The mixture was further stirred at an internal temperature of 15° to 20° C. for 2 hours and a solution containing 20 g of sodium hydrogen carbonate in 100 ml of water was added. The reaction mixture was stirred at room temperature for 10 hours and, then, filtered. After phase separation, the water layer was further extracted with 100 ml of ethyl acetate and the organic layers were combined, dried over anhydrous sodium sulfate, filtered, and concentrated under reduced pressure to give 6.96 g of oil. This oil was purified by silica gel column chromatography (hexane/acetone=3/1) to provide 1.97 g (7 mmols, yield 35%) of (2S,3S)-3-(t-butoxycarbonylamino)-4-phenylbutane-1,2-diol. $^1$H-NMR (CDCl$_3$)δ/ppm: 1.35 (s, 9H), 2.80–3.15 (m,2H), 3.34–3.45 (m, 1H), 3.60–3.72 (m, 2H), 3.80–3.90 (m, 1H), 4.50 (brs, 1H), 7.15–7.40 (m,5H)

IR (KBr)cm$^{-1}$: 3360, 1690, 1525, 1170, 1015

EXAMPLE 7

Production of (2R,3R)-3-(t-butoxycarbonylamino)-4-phenylbutane-1,2-diol

The reaction procedure of Example 6 was repeated except that 4.99 g (20 mmols) of D-N-(t-butoxycarbonyl)phenylalaninal was used in lieu of 4.99 g of L-N-(t-butoxycarbonyl)phenylalaninal and the reaction product was purified by silica gel column chromatography to provide 1.85 g (6.58 mmols, yield 32.9%) of (2R,3R)-3-(t-butoxycarbonylamino)-4-phenylbutane-1,2-diol.

$^1$H-NMR (CDCl$_3$)δ/ppm: 1.35 (s, 9H), 2.80–3.16 (m,2H), 3.35–3.45 (m, 1H), 3.60–3.73 (m, 2H), 3.80–3.90 (m, 1H), 4.50 (brs, 1H), 7.15–7.40 (m, 5H)

IR (KBr)cm$^{-1}$: 3360, 1690, 1525, 1170, 1015

EXAMPLE 8

Production of (4S,5S)-5-hydroxymethyl-4-phenylmethyloxazolidinone

In 20 ml of THF was dissolved 400 mg (1.27 mmols) of (2S,3S)-3-(benzyloxycarbonylamino)-4-phenylbutane-1,2-diol and the solution was cooled to 0° C. Then, 76.2 mg (1.91 mmols) of 60% sodium hydroxide was added and while the temperature was allowed to return to room temperature, the mixture was stirred for another 30 minutes. Then, 50 ml of saturated aqueous ammonium chloride solution was added and the reaction mixture was extracted with ethyl acetate. The extract was dried over sodium sulfate, filtered, and concentrated under reduced pressure to give 285 mg of oil. This oil was purified by silica gel column chromatography (hexane/ethyl acetate=2/1) to provide 169.1 mg (0.82 mmol, yield 65%) of (4S,5S)-5-hydroxymethyl-4-phenylmethyl-2-oxazolidinone as crystals.

$^1$H-NMR (DMSO-d$_6$)δ/ppm: 2.66, 2.91 (2dd, 2H, J=13.5, 5.5 and 8.5 Hz), 3.63 (m, 2H), 4.13 (dt, 1H, J=5.5, 8.5 and 8 Hz), 4.52 (dt, 1H, J=8 and 5 Hz), 5.00 (s, 1H), 7.15–7.33 (m, 5H), 7.50 (brs, 1H)

IR (KBr)cm$^{-1}$: 3340, 3260, 1725, 1040

EXAMPLE 9

Production of (4S,5S)-5-hydroxymethyl-4-phenylmethyloxazolidinone

In 20 ml of THF was dissolved 400 mg (1.27 mmols) of (2S,3S)-3-(benzyloxycarbonylamino)-4-phenylbutane-1,2-diol and the solution was cooled to 0° C. Then, 171 mg (1.52 mmols) of potassium t-butoxide was added to the above solution. While the temperature was allowed to return to room temperature, the mixture was further stirred for 30 minutes. After addition of 50 ml of saturated aqueous ammonium chloride solution, the reaction mixture was extracted with ethyl acetate. The extract was dried over sodium sulfate, filtered, and concentrated under reduced pressure to give 290 mg of oil. This oil was purified by silica gel column chromatography (hexane/ethyl acetate=2/1) to provide 225.9 mg (1.09 mmols, yield 86%) of (4S,5S)-5-hydroxymethyl-4-phenylmethyloxazolidinone as crystals.

The spectrometric data of this compound were in good agreement with those of the compound of Example 8.

EXAMPLE 10

Production of (4S,5S)-5-hydroxymethyl-4-phenylmethyloxazolidinone

The reaction procedure of Example 9 was repeated except that 434 mg (1.27 mmols) of (2S,3S)-3-(t-butoxycarbonylamino) -4-phenylbutane-1,2-diol was used in lieu of 400 mg (1.27 mmols) of (2S,3S)-3-(benzyloxycarbonylamino)-4-phenylbutane-1,2-diol and the reaction product was purified by silica gel column chromatography (hexane/ethyl acetate=2/1) to provide 183 mg (0.887 mmol, yield 70%) of (4S,5S)-5-hydroxymethyl-4-phenylmethyloxazolidinone as crystals.

The spectrometric data of this compound were in good agreement with those of the compound of Example 8.

EXAMPLE 11

Production of (4R,5R)-5-hydroxymethyl-4-phenylmethyloxazolidinone

The reaction procedure of Example 9 was repeated except that 400 mg (1.27 mmols) of (2R,3R)-3-(benzyloxycarbonylamino)-4-phenylbutane-1,2-diol was used in lieu of 400 mg (1.27 mmols) of (2S,3S)-3-(benzyloxycarbonylamino)-4-phenylbutane-1,2-diol and the reaction product was purified by silica gel column chromatography (hexane/ethyl acetate=2/1) to provide (183 mg (0.887 mmol, yield 70%) of (4R,5R)-5-hydroxymethyl-4-phenylmethyloxazolidinone as crystals.

$^1$H-NMR (DMSO-d$_6$)δ/ppm: 2.65, 2.90 (2dd, 2H, J=13.5, 5.5 and 8.5 Hz), 3.62 (m, 2H), 4.13 (dt, 1H, J=5.5, 8.5 and 8 Hz), 4.51 (dt, 1H, J=8 and 5 Hz), 5.00 (s, 1H), 7.15–7.33 (m, 5H), 7.50 (brs, 1H)

IR (KBr)cm$^{-1}$: 3340, 3260, 1725, 1040

INDUSTRIAL APPLICABILITY

The present invention provides an efficient commercial method for producing 3-amino-2-hydroxy-1-propanol derivatives and oxazolidinone derivatives derived therefrom, which are of value as intermediates for the production of medicines such as HIV protease inhibitors.

We claim:

1. A process for producing an 3-amino-2-hydroxy-1-propanol compound of the formula (2)

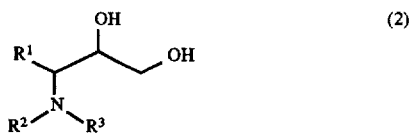

(2)

wherein $R^1$, $R^2$ and $R^3$ are as defined below characterized in that an aminoaldehyde compound of the formula (1)

(1)

wherein $R^1$ represents aralkyl; $R^2$ and $R^3$ independently represent hydrogen or an amino-protecting group; provided, however that at least one of $R^2$ and $R^3$ is an amino protecting group and a formaldehyde source are subjected to hetero-coupling reaction in the presence of a low valence titanium formed by reducing $TiCl_4$ or $TiCl_3$ with Zn, Zn—Cu, Mg or Al in the reaction system, wherein said hetero-coupling reaction is carried out at a temperature of from −50° to 40° C. at a concentration of said aminoaldehyde compound of the formula (1) of 1 to 20 w/v%: and said formaldehyde source being used in a proportion of 1 to 50 molar equivalents, said $TiCl_4$ or $TiCl_3$ being used in a proportion of 0.1 to 5 molar equivalents, and said Zn, Zn—Cu, Mg or Al being used in a proportion of 1 to 6 molar equivalents to said aminoaldehyde compound of the formula (1).

2. The process for producing an 3-amino-2-hydroxy-1-propanol compound as claimed in claim 1 wherein said formaldehyde source is paraformaldehyde, formalin, trioxane or polyoxymethylene.

3. The process for producing an 3-amino-2-hydroxy-1-propanol compound as claimed in claim 1 wherein said aminoaldehyde compound of the formula (1) is (L)-N-(benzyloxycarbonyl)phenylalaninal or (D)-N-(benzyloxycarbonyl)phenylalaninal and said 3-amino-2-hydroxy-1-propanol compound of the formula (2) is (2S,3S)-3-(benzyloxycarbonylamino)-4-phenylbutane-1, 2-diol or (2R,3R)-3-(benzyloxycarbonylamino)-4-phenylbutane-1,2-diol as the case may be with stereoselectivity.

4. The process for producing an 3-amino-2-hydroxy-1-propanol compound as claimed in claim 1 wherein said aminoaldehyde compound of the formula (1) is either (L)-N-(t-butoxycarbonyl)phenylalaninal or (D)-N-(t-butoxycarbonyl)phenylalaninal and said 3-amino-2-hydroxy-1-propanol compound is (2S,3S)-3-(t-butoxycarbonylamino)-4-phenylbutane-1,2-diol or (2R,3R)-3-(t-butoxycarbonylamino)-4-phenyl butane-1,2-diol as the case may be with stereoselectivity.

5. The process for producing an 3-amino-2-hydroxy-1-propanol compound as claimed in claim 3 wherein said aminoaldehyde compound of the formula (1) is (L)-N-(benzyloxycarbonyl)phenylalaninal or (D)-N-(benzyloxycarbonyl)phenylalaninal and said 3-amino-2-hydroxy-1-propanol compound of the formula (2) is (2S,3S)-3-(benzyloxycarbonylamino)-4-phenylbutane-1,2-diol or (2R,3R)-3-(benzyloxycarbonylamino)-4-phenylbutane-1,2-diol as the case may be with stereoselectivity.

6. The process for producing an 3-amino-2-hydroxy-1-propanol compound as claimed in claim 3 wherein said aminoaldehyde compound of the formula (1) is either (L)-N-(t-butoxycarbonyl)phenylalaninal or (D)-N-(t-butoxycarbonyl)phenylalaninal and said 3-amino-2-hydroxy-1-propanol compound is (2S,3S)-3-(t-butoxycarbonylamino)-4-phenylbutane-1,2-diol or (2R,3R)-3-(t-butoxycarbonylamino)-4-phenyl butane-1,2-diol as the case may be with stereoselectivity.

* * * * *